US008029944B2

(12) United States Patent
Yau et al.

(10) Patent No.: US 8,029,944 B2
(45) Date of Patent: Oct. 4, 2011

(54) USE OF SILICON PARTICLES AS CATALYST, ELECTROCHEMICAL DEVICE COMPRISING THE PARTICLES AND METHOD THEREOF

(75) Inventors: Siu-Tung Yau, Solon, OH (US); Munir H. Nayfeh, Urbana, IL (US); Gang Wang, Lowell, MA (US)

(73) Assignee: Cleveland State University, Cleveland, OH (US)

( * ) Notice: Subject to any disclaimer, the term of this patent is extended or adjusted under 35 U.S.C. 154(b) by 711 days.

(21) Appl. No.: 12/124,870

(22) Filed: May 21, 2008

(65) Prior Publication Data

US 2009/0011295 A1  Jan. 8, 2009

Related U.S. Application Data

(60) Provisional application No. 60/931,065, filed on May 21, 2007.

(51) Int. Cl.
*H01M 4/90* (2006.01)
*H01M 8/22* (2006.01)

(52) U.S. Cl. ......... 429/523; 429/504; 429/505; 429/506

(58) Field of Classification Search .................. 429/413, 429/523, 504, 505, 506; 423/652; 204/192.1
See application file for complete search history.

(56) References Cited

U.S. PATENT DOCUMENTS

2006/0127708 A1* 6/2006 Ping et al. .................. 429/12
2007/0036713 A1* 2/2007 Kobayashi et al. ........... 423/652

OTHER PUBLICATIONS

International Search Report for International Application No. PCT/US2008/064390, Aug. 12, 2008.
Debra R. Rolison, et al., "Catalytic Nanoarchitectures—the Importance of Nothing and the Unimportance of Periodicity," *Science*, vol. 299, 1698 (2003).
M. Valden, X Lai, D. W. Goodman, "Onset of Catalytic Activity of Gold Clusters on Titania with the Appearance of Nonmetallic Properties," *Science*, New Series, vol. 281, No. 5383, 1647 (Sep. 11, 1998).
Antonino Salvatore Aricò, Peter Bruce, Bruno Scrosati, Jean-Marie Tarascon and Walter Van Schalkwijk, "Nanostructured materials for advanced energy conversion and storage devices," *Nature Materials*, vol. 4, 366 (May 2005).
Guangli Che, Brinda B. Lakshmi, Ellen R. Fisher and Charles R. Martin, "Carbon nanotubule membranes for electrochemical energy storage and production," *Nature*, vol. 393, 346 (1998).
W. Vielstich, H. A. Gasteiger, A. Lamm, Eds., *Handbook of Fuel Cells—Fundamentals, Technology and Applications*, vol. 2: Electrocatalysis (John Wiley & Sons, Ltd., 2003).

(Continued)

*Primary Examiner* — Jonathan Crepeau
*Assistant Examiner* — Kenneth Douyette
(74) *Attorney, Agent, or Firm* — Fay Sharpe LLP

(57) ABSTRACT

The invention provides the use of silicon particles as redox catalyst, an electrochemical device and method thereof. As electrocatalyst, the silicon particles catalyze a redox reaction such as oxidization of the redox reactant such as renewable fuels e.g. methanol, ethanol and glucose. The device such as a fuel cell comprises a redox reactant and a catalytic composition comprising silicon nanoparticles. The silicon particles catalyze the redox reaction on an electrode such as anode in the device. In preferred embodiments, the electrocatalysis is dramatically improved under low illuminance such as in darkness. The invention can be widely used in applications related to for example a fuel cell, a sensor, an electrochemical reactor, and a memory.

15 Claims, 17 Drawing Sheets

OTHER PUBLICATIONS

Erik Reddington, Anthony Sapienza, Bogdan Gurau, Rameshkrishnan Viswanathan, S. Sarangapani, Eugene S. Smotkin, Thomas E. Mallouk, "Combinatorial Electrochemistry: A Highly Parallel, Optical Screening Method for Discovery of Better Electrocatalysts," *Science*, New Series, vol. 280, No. 5370, 1735 (Jun. 12, 1998).

M. Watanabe and S. Motoo, "Electrocatalysis by Ad-Atoms, Part I. Enhancement of the Oxidation of Methanol on Platinum and Palladium by Gold Ad-Atoms," *Electroanalytical Chemistry and Interfacial Electrochemistry*, 60, 259 (1975).

Steven G. Chalk, James F. Miller, "Key challenges and recent progress in batteries, fuel cells, and hydrogen storage for clean energy systems," *Journal of Power Sources*, 159, 73 (2006).

Gennadiy Belomoin, Joel Therrien, and Munir Nayfeh, "Oxide and hydrogen capped ultrasmall blue luminescent Si nanoparticles," *Applied Physics Letters*, vol. 77, No. 6, 779 (Aug. 7, 2000).

S. Rao, J. Sutin, R. Clegg, E. Gratton, M. H. Nayfeh, S. Habbal, A. Tsolakidis and R. M. Martin, "Excited states of tetrahedral single-core $Si_{29}$ nanoparticles," *Physical Review B* 69, 205319 (2004).

M. H. Nayfeh, O. Akcakir, G. Belomoin, N. Barry, J. Therrien, and E. Gratton, "Second harmonic generation in microcrystallite films of ultrasmall Si nanoparticles," *Applied Physics Letters*, vol. 77, No. 25, 4086 (Dec. 18, 2000).

M. H. Nayfeh, S. Rao, N. Barry, J. Therrien, G. Belomoin, and A. Smith, "Observation of laser oscillation in aggregates of ultrasmall silicon nanoparticles," *Applied Physics Letters*, vol. 80, No. 1, 121 (Jan. 7, 2002).

Gang Wang, Kevin Mantey, Munir H. Nayfeh and Siu-Tung Yau, "Enhanced amperometric detection of glucose using $Si_{29}$ particles," *Applied Physics Letters* 89, 243901 (2006).

J. Therrien, "Size dependence of the electrical characteristics of silicon nanoparticles," University of Illinois at Urbana-Champaign (2002).

* cited by examiner

USE OF SILICON PARTICLES AS CATALYST, ELECTROCHEMICAL DEVICE COMPRISING THE PARTICLES AND METHOD THEREOF

This application claims priority upon U.S. provisional patent application Ser. No. 60/931,065 filed May 21, 2007, which is incorporated herein by reference.

BACKGROUND OF THE INVENTION

The present invention relates to the use of silicon particles as a redox catalyst, an electrochemical device including the silicon particles and method thereof. It finds particular application in conjunction with a redox catalyst, an energy-generation device such as a fuel cell, a sensor, an electrochemical reactor, and a memory, and will be described with particular reference thereto. However, it is to be appreciated that the present exemplary embodiment is also amenable to other like applications.

Fuel cell technology is viewed as an increasingly important alternative means for generation of energy. To utilize nature's renewable energy sources such as various kinds of organic fuel, new electrocatalysts, especially those with novel properties due to their dimensions on the nanoscale, need to be developed in order to meet the requirements imposed by fuel cell applications, as described in D. R. Rolison, Science 299, 1698 (2003); M. Valden, X. Lai, D. W. Goodman, Science 281, 1647 (1998); A. S. Arico, P. Bruce, B. Scrosati, J.-M. Tarascon, W. V. Schalkwijk, Nature Materials 4, 366 (2005); and G. Che, B. B. Lakshmi, E. R. Fisher, C. R. Martin, Nature 393, 346 (1998).

Platinum-based noble metals are currently used in commercial fuel cells as the anode material to achieve electrocatalysis (electro-oxidation) of methanol and ethanol. Publications such as W. Vielstich, H. A. Gasteiger, A. Lamm, Eds., Handbook of fuel cells—fundamentals, technology and applications, vol. 2 (John Wiley & Sons, 2003), pp and E. Reddington et al., Science 280, 1735 (1998) have disclosed the use of bimetallic electrocatalyst systems based on rare/precious metals such as the platinum-ruthenium (Pt—Ru) alloy, which have been widely used as the anode electrode for direct electro-oxidation of methanol in direct methanol fuel cells. According to M. Watanabe, S. Motoo, J. Electroanal. Chem. 60, 259 (1975), the binary alloys offer a "bi-functional mechanism", in which Pt breaks the C—H bonds of methanol and Ru promotes water discharge and removes adsorbed CO species in order to reduce electrode poisoning.

Although fuel cells based on binary alloys are commercially available, the high cost of precious metals and their limited supply make this kind of fuel cell economically unviable, as realized by S. G. Chalk, J. F. Miller, Journal of Power Sources 159, 73 (2006). Moreover, the acute and chronic toxicity of Ruthenium is not fully known. However, since oxidation of Ruthenium forms the highly toxic and volatile ruthenium oxide, the portable use and disposal of the alloy-based fuel cells will cause safety and environmental concerns. In addition, electrode poisoning is also a major problem affecting the performance of present fuel cells.

Enzymes are used for the construction of sensors. However, enzymes are not only expensive; their stability is also a major problem for long-term implantable applications.

Advantageously, the present invention provides the use of silicon particles as a redox catalyst, an electrochemical device comprising the silicon particles and method thereof, which overcome the afore-mentioned problem. For example, the electrochemical device uses silicon particles which are inexpensive and non-poisonous; and it uses particle-immobilized electrode that does not induce electrode poisoning.

BRIEF DESCRIPTION OF THE INVENTION

One aspect of the invention provides a method of conducting a redox reaction, which comprises using silicon particles as a catalyst.

Another aspect of the invention provides an electrochemical device comprising:
a redox reactant, and
a catalytic composition comprising silicon particles,
wherein the silicon particles catalyze a redox reaction of the redox reactant.

Still another aspect of the invention provides a method of conducting a redox reaction in an electrochemical device, which comprises:
(1) providing an electrochemical device comprising a redox reactant subject to a redox reaction; and
(2) catalyzing the redox reaction with a catalytic composition comprising silicon particles.

DETAILED DESCRIPTION OF THE INVENTION

Figure 1A:
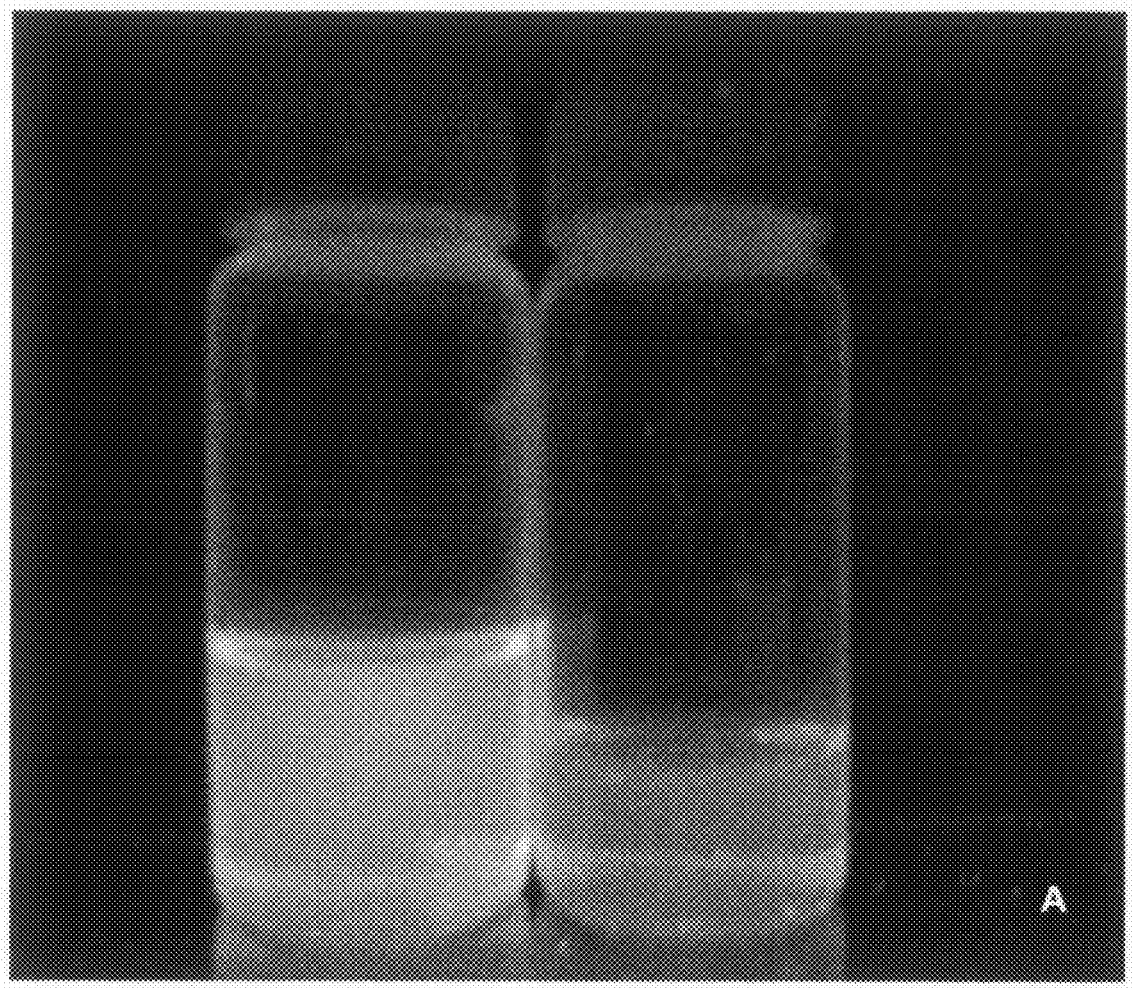
FIGS. 1A-C show the visible emission and electron micrographs of two kinds of silicon nanoparticles (1 nm and 2.8 nm) in an embodiment of the invention.

The term "redox reaction" is defined as a reduction/oxidation reaction in which atoms have their oxidation number (oxidation state) changed. Oxidation means an increase in oxidation number, and reduction means a decrease in oxidation number.

The term "redox reactant" is defined to include (1) oxidizing agents, oxidants or oxidizers that are oxidative and have the ability to oxidize other substances; and (2) reducing agents, reductants or reducers that are reductive and have the ability to reduce other substances.

In many embodiments of the invention, the redox reaction in the electrochemical device involves the transfer of one or more electrons between an oxidizing agent and a reducing agent. As electro-catalyst, the silicon particles in the catalytic composition catalyze the redox reaction (electrocatalysis).

In addition to silicon particles, the catalytic composition may comprise other catalytic or noncatalytic material(s) which, for example, can be used on or with an electrode for catalysis applications.

In certain embodiments, the silicon particles comprise silicon nanoparticles, e.g. colloidal silicon nanoparticles. The size of the silicon particles can be generally in the range of from about 0.1 nm (nanometer) to about 100 nm, preferably in the range of from about 0.5 nm to about 20 nm, and more preferably in the range of from about 1.0 nm to about 2.8 nm, as measured with transmission electron microscopy.

In exemplary embodiments, 1-nanometer and 2.8-nanometer silicon particles were used as electro-catalysts for redox reactants such as renewable fuels e.g. methanol, ethanol and glucose.

In a specific embodiment, the silicon nanoparticles were made by electrochemical etching of a (100)-oriented p-type (1-10 Ω-cm) silicon wafer in hydrofluoric acid and hydrogen peroxide followed by shaking off the particles from the etched wafer using ultrasound in water or organic solvents such as benzene, isopropyl alcohol and tetrahydrofuran (THF) to form a colloid (see also G. Belomoin, J. Therrien, M. Nayfeh, *Appl. Phys. Lett.* 77, 779 (2000)). This etching technique was used to prepare the 1-nanometer particles (Si1) and the 2.8-nanometer particles (Si2.8), subject to different etching conditions.

Monte Carlo simulation of the Si1 particle suggested a filled fullerene structure of $Si_{29}H_{24}$, in which a central core silicon atom and four other silicon atoms were arranged in a tetrahedral coordination and the 24 remaining silicon atoms had undergone a H-terminated bulk-like (2×1) reconstruction of dimer pairs on (001) facets (6 reconstructed surface dimers) (See S. Rao et al., *Phys. Rev. B* 69, 205319 (2004)). The particles have exhibited optical properties such as luminescence in the visible part of the spectrum (see G. Belomoin, J. Therrien, M. Nayfeh, *Appl. Phys. Lett.* 77, 779 (2000)), second harmonic generation (see M. H. Nayfeh et al., *Appl. Phys. Lett.* 77, 4086 (2000)) and laser oscillation (see M. H. Nayfeh et al., *App. Phys. Lett.* 80, 121 (2002)).

Figure 1B:
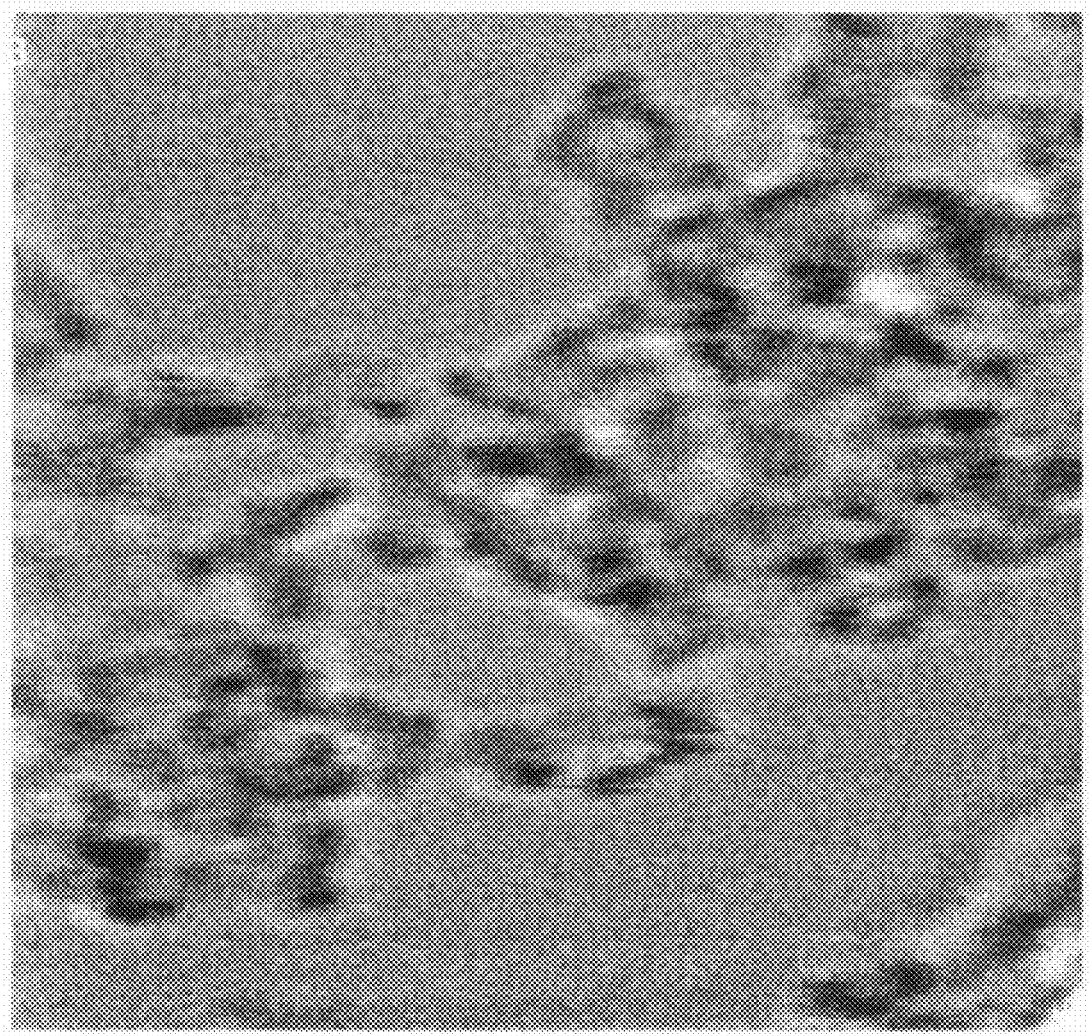
Figure 1C:
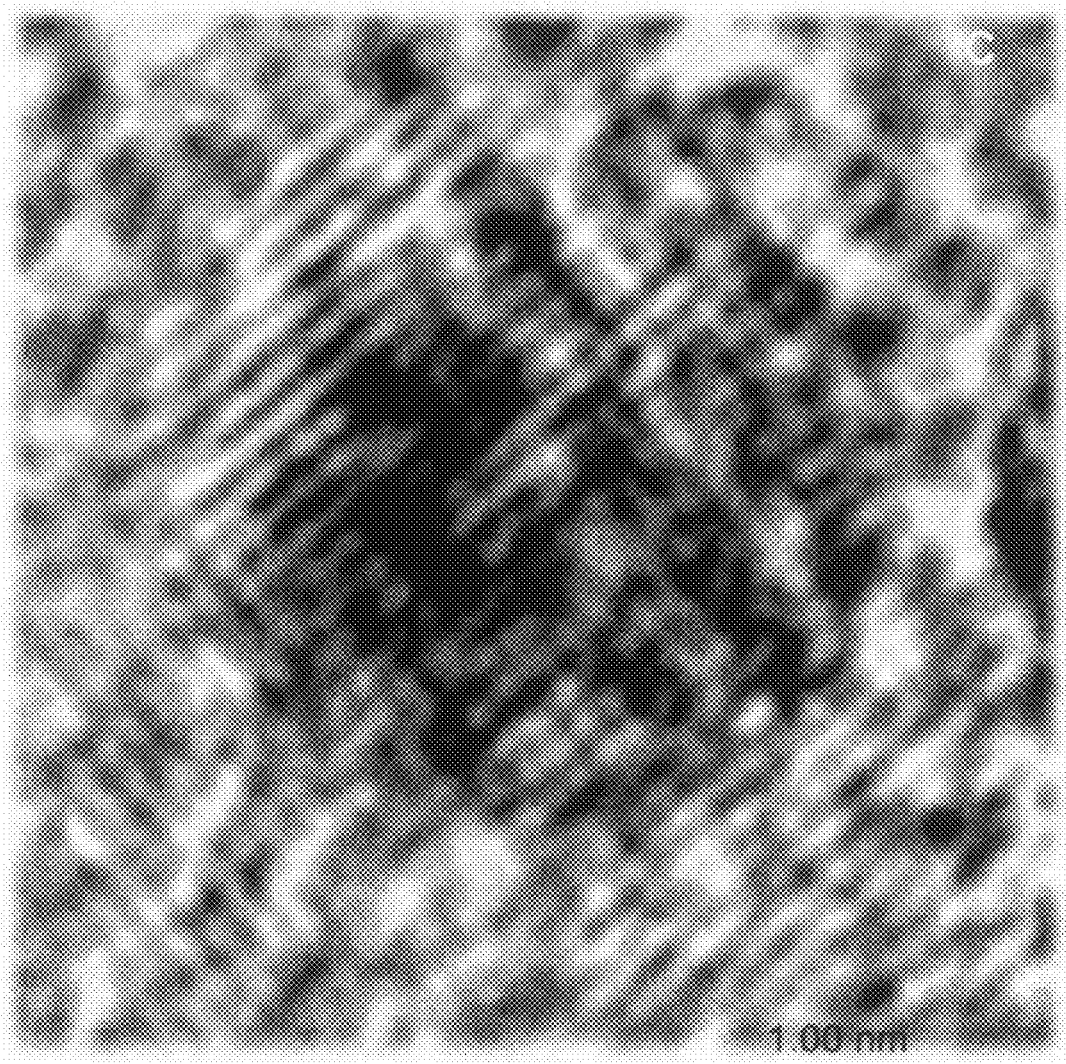

The silicon particles of the invention exhibit visible emission under UV radiation. FIG. 1 shows the spontaneous emission and electron micrographs of the 1-nm and the 2.8-nm silicon particles. When excited by UV radiation, the 1-nm particles in the bottle (left) emit blue light and the 2.8-nm particles in the bottle (right) emit red light. It is believed that under UV excitation, the Si1 particle generates blue spontaneous emission with a measured band-gap of 3.5 eV and the Si2.8 particle generates red emission with a 2 eV band-gap. FIG. 1B shows the electron micrograph of the 1-nm silicon particles, in which each dark region has a size of 1 nm, indicating a single particle. FIG. 1C shows the electron micrograph of a single 2.8-nm particle.

Any redox reactant can be used in the electrochemical device of the invention, if its nature permits the catalytic composition comprising silicon particles as described above to catalyze one or more of its redox reactions. Redox reactants include organic compounds, for example, methanol, ethanol, glucose, hydrocarbon such as methane, the blood ketone 3β-hydroxybutyrate (3β-OHB), phenol, dopamine, lactose, and fructose etc. and redox reactants such as inorganic compounds, for example, sodium nitrite, in solution form and in gaseous form, can be oxidized using the catalytic composition.

In exemplary embodiments, the redox reactant comprises an organic fuel or a mixture of organic fuels. Examples of organic fuels include, but are not limited to, methanol, ethanol and glucose.

In various embodiments, the electrochemical device of the invention further comprises an electrode. The electrode may be an anode, with which the redox reactant is oxidized. For example, when the electrode is used as the anode of a fuel cell, it will bring about the oxidation of redox reactants such as methanol, ethanol and glucose with the help of the catalytic ability of a catalytic composition comprising silicon particles, and enables the fuel cell to convert chemical energy to electrical energy. Examples of suitable electrodes include, but are not limited to, silicon electrodes, graphite electrodes, and carbon paper electrodes.

In specific embodiments, silicon, graphite, carbon cloth, and carbon paper were used as the electrodes to support the silicon nanoparticles for electrochemical characterization. The silicon electrodes can be made of or from n-type or p-type silicon wafer with suitable resistivity ρ. In exemplary embodiments, the silicon electrodes were n-type silicon wafers with resistivity $\rho < 0.005$ Ω-cm.

In various embodiments, the silicon particles are engaged with the electrode. For example, the particles can be immobilized on the electrode surface using different methods.

In embodiments, the particles can be mixed with a polymer and the mixture is then deposited on the electrode to increase the adhesion of the particle to the electrode. Alternatively, the particle's surface can be modified by attaching other molecules so that the modified particles can be better attached to the electrode.

In a specific embodiment, the particles were simply attached to the bare electrode surface. For example, in preparing particle-immobilized silicon electrodes, silicon wafers were cleaned with ethanol, isopropanol and de-ionized water. The wafer surface was covered with a mask to achieve a working area of, for example, about 1 mm×1 mm. A 0.1 ml drop of the colloid was spread on the exposed wafer surface, and the sample was incubated for 10 hours, and then rinsed with de-ionized water. Atomic force microscopy of the electrode surface showed the presence of the particles at a sub-monolayer level (see also G. Wang, K. Mantey, M. H. Nayfeh, S.-T. Yau, *Appl. Phys. Lett.* 89, 243901 (2006)). Two kinds of silicon electrode were made, one of which was silicon wafers immobilized with the Si1 particle (the Si1-Si electrode) and another was silicon wafers immobilized with the Si2.8 particle (the Si2.8-Si electrode).

Particle-immobilized graphite electrodes (similarly abbreviated as Si1-G electrode and the Si2.8-G electrode) were made by incubating the silicon particles on, for example, a disc of graphite having a surface area of 7 mm².

The particle-immobilized electrodes were used as the working electrode in a typical three-electrode electrochemical cell for voltammetry measurements. An Ag/AgCl electrode was used as the reference electrode, and a platinum wire was used as the counter electrode. Redox reactants whose oxidation was to be catalyzed using the particle-immobilized electrodes were dissolved in a buffer solution and introduced into the cell for measurements. The result of the voltammetric measurements was found to be independent of the presence of molecular oxygen.

The electrochemical responses of the two kinds of particle-immobilized electrode to methanol, ethanol and glucose have been investigated. Oxidation of the three fuels can be indicated by electromechanical characterization. Bare silicon wafers and graphite showed no electrochemical response to the redox reactants tested in the invention up to a potential as high as 1.6 V.

Figure 2A:
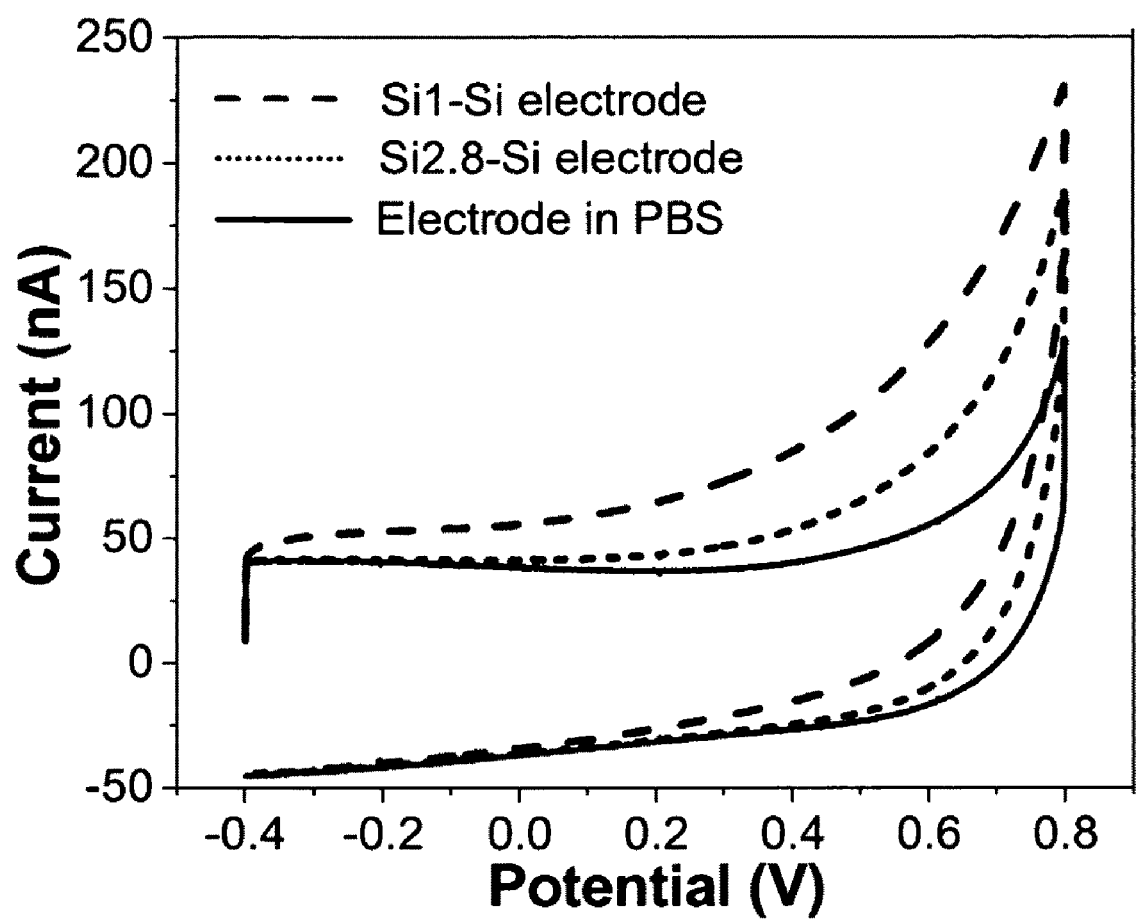
FIGS. 2A-B show the onset potential of oxidation as a function of particle size and the calibration curves of particle samples for ethanol and methanol as characterized and measured using cyclic voltammetry (CV)
Figure 2B:
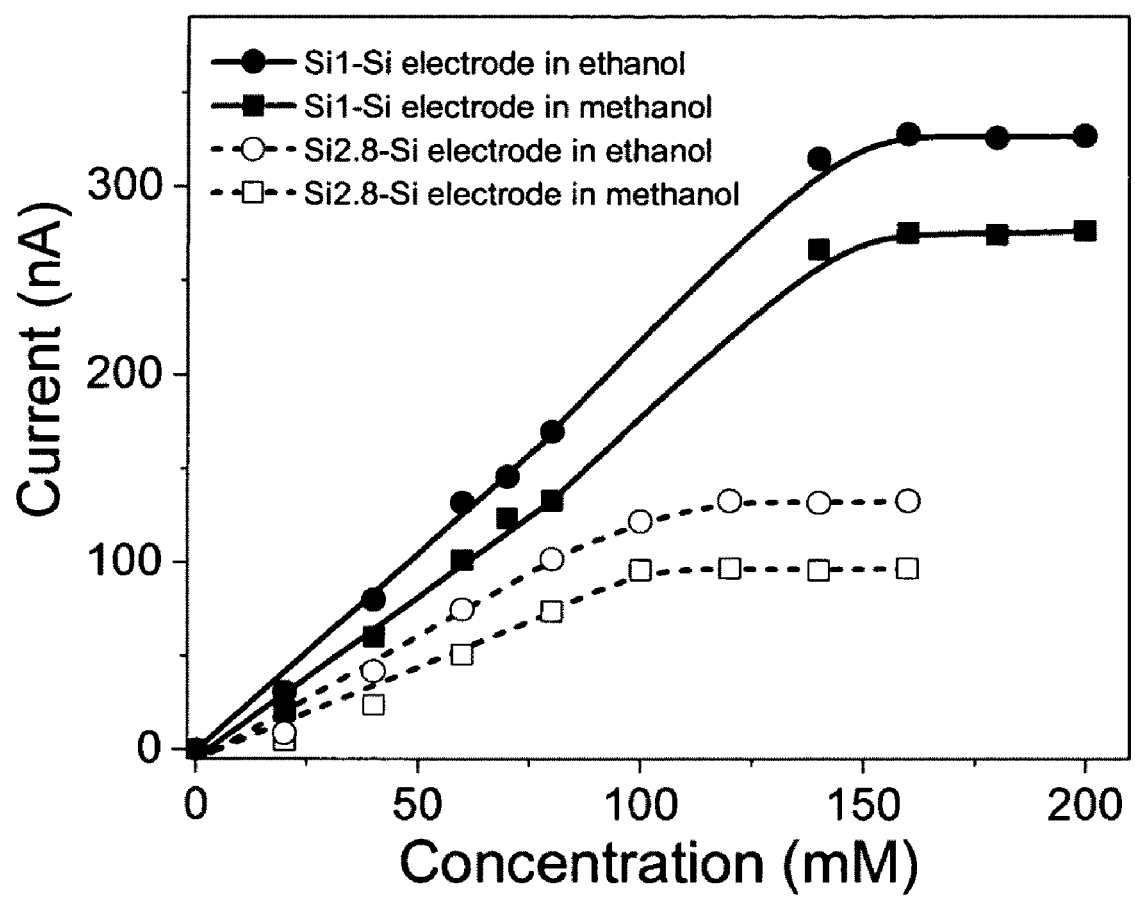

FIG. 2 shows the onset potential of oxidation as a function of particle size and the calibration curves of particle samples for ethanol and methanol. FIG. 2A demonstrates that the onset potential of oxidation depends on particle size. At pH 7, the 1-nm particle shows an onset of electro-oxidation for ethanol at −0.4 V vs. Ag/AgCl. The onset of the 2.8-nm particle is 0.1 V vs. Ag/AgCl. FIG. 2B shows the calibration curves of the two kinds of particles for ethanol and methanol.

FIG. 3 shows electrochemical characterization of the particle-immobilized electrodes. FIG. 3A shows CVs of a Si2.8-Si electrode in PBS at pH 7 and in the same PBS containing 120 mM methanol. FIG. 3B shows calibration curves of the Si2.8-Si electrode for ethanol, methanol and glucose at pH 7. The curves were obtained at a potential of 0.8 V. FIG. 3C shows the CV of a graphite electrode obtained in PBS which is displayed with those of a Si2.8-G electrode obtained in PBS and ethanol. All curves were obtained at pH 7. Two new oxidation peaks appear at high ethanol concentrations. FIG. 3D shows calibration curves of the Si2.8-G electrode for ethanol and methanol at pH 7. The curves were obtained at the potential of 0.55 V, where the first new oxidation peak is located.

Figure 3A:
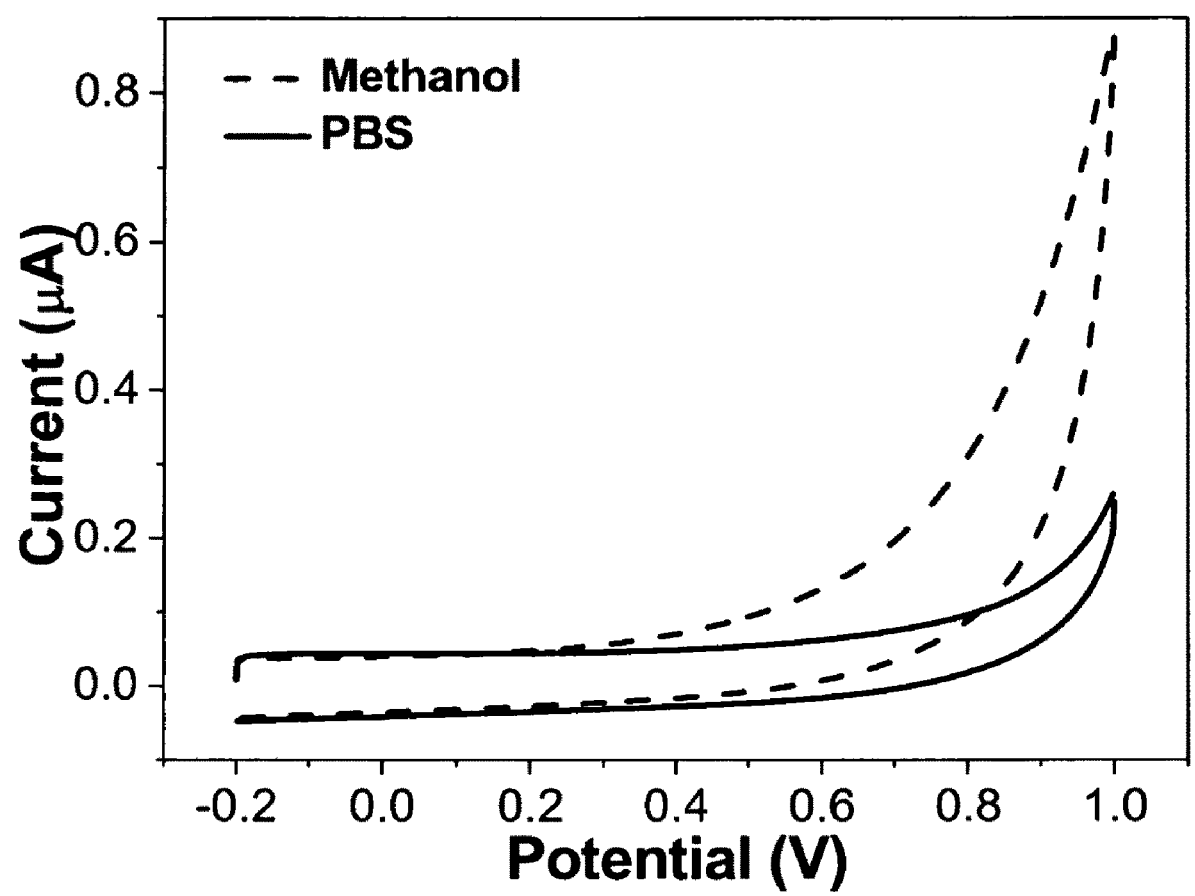
FIGS. 3A-D show the electrochemical characterizations of some particle-immobilized electrodes in an embodiment of the invention.

The cyclic voltammograms (CV) of a Si2.8-Si electrode obtained in methanol are shown in FIG. 3A. The figure shows the CV of the electrode obtained in a phosphate buffer solution (PBS) at pH 7 without methanol and the CV obtained with 120 mM of methanol dissolved in the PBS. The increase in the anodic current due to methanol above the background in the positive potential polarity indicates that methanol is oxidized by the electrode. A similar effect was also obtained with the Si1-Si electrode. Generally the Si1-Si electrode generates a greater anodic current for the fuels tested. Because the bare silicon wafer shows no response to methanol, the silicon particles exhibit a catalytic character in the electro-oxidation of methanol.

Figure 3B:
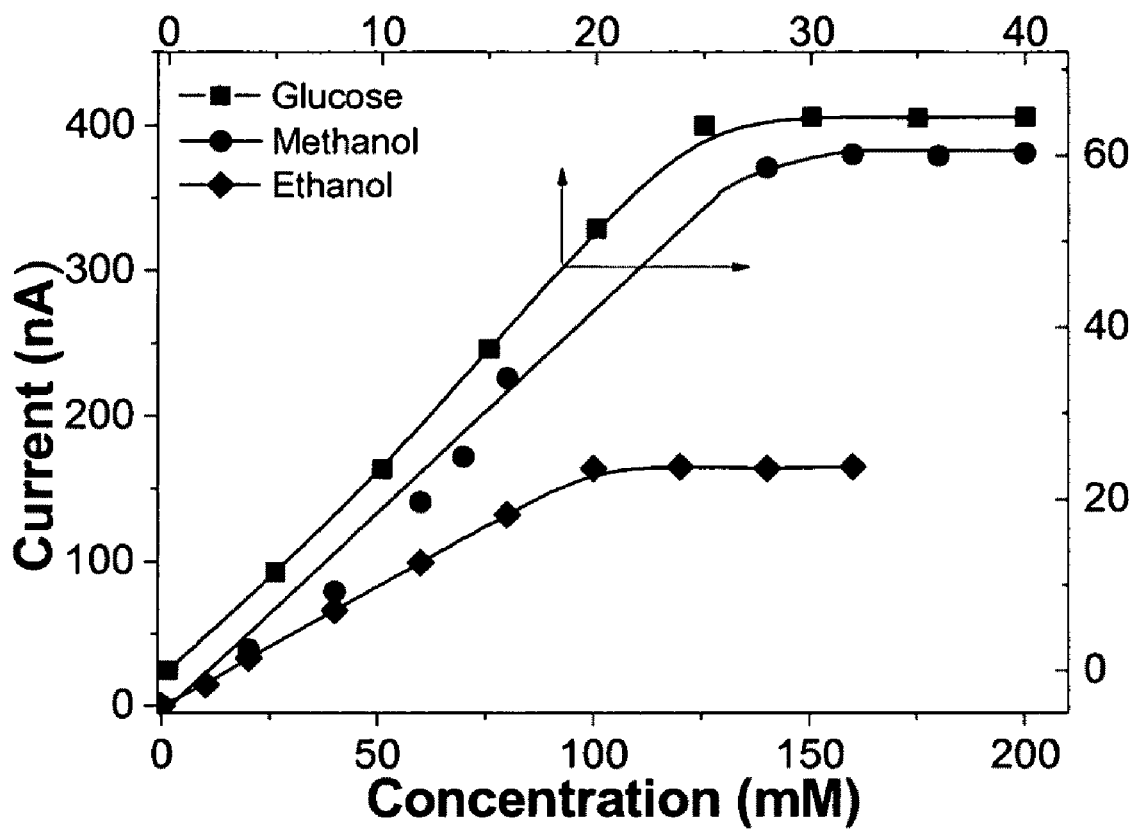

FIG. 3B shows the calibration curve of the Si2.8-Si electrode for methanol. The electrochemical responses of the Si1-Si electrode and the Si2.8-Si electrode to ethanol and glucose all show similar catalytic effect that, when the fuel is introduced to the electrode, the anodic current starts to increase for potentials greater than 0.3 V. The calibration curves of the Si2.8-Si electrode for the two fuels are also shown in FIG. 3B. The calibration curves were obtained using three Si2.8-Si electrodes, on which the particle coverage may be different. The shape of the calibration curves, i.e. a linear region at low fuel concentrations followed a saturation region at higher concentrations, resembles that of enzymes and is indicative of the Michaelis-Menten kinetics, which implies the limited amount of particle (the catalytic unit) on the electrode. The monotonous increase of the electrodes' anodic current in response to the fuels suggests a direct catalysis pathway: the fuel molecules are oxidized due to the presence of the particle so that electrons are transferred from the molecules to the electrode.

Figure 3C:
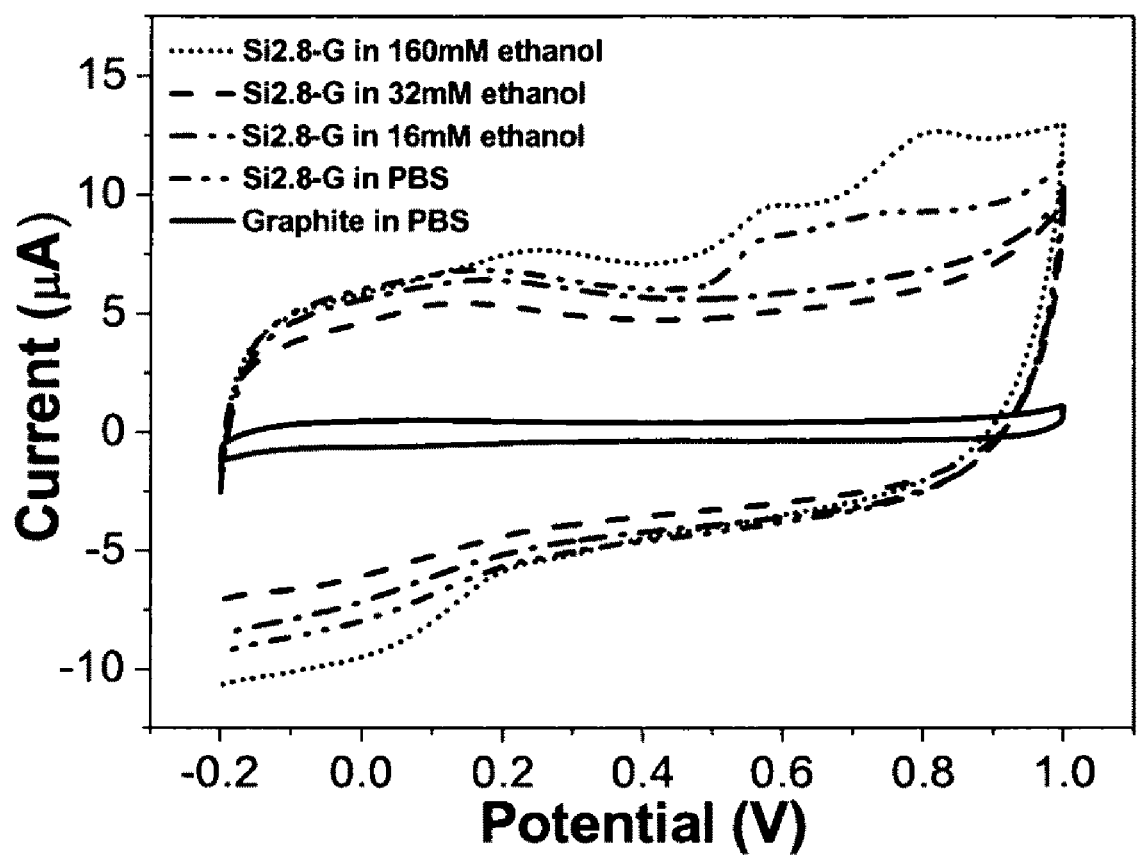
Figure 3D:
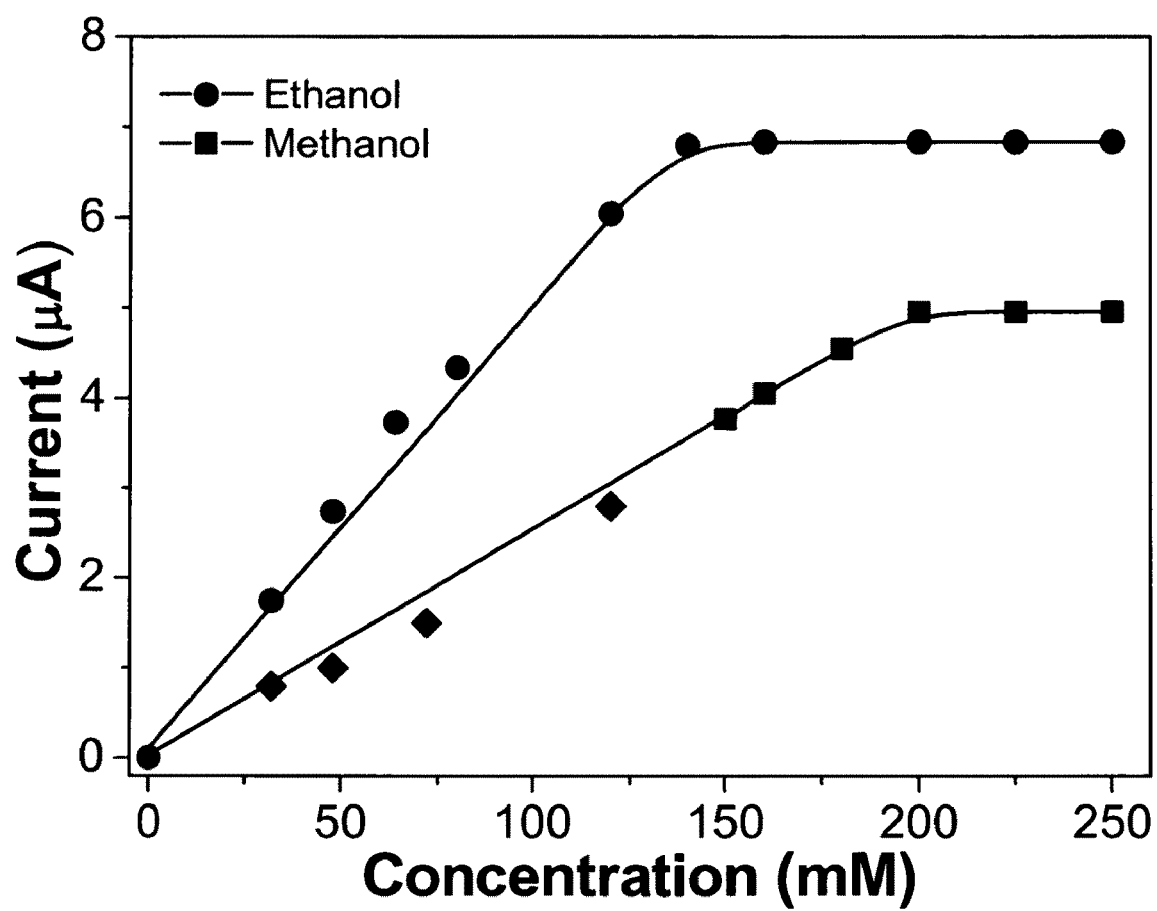

The particle-immobilized graphite electrodes exhibit a complex catalytic characteristic as demonstrated in FIG. 3C. The CV of the bare graphite electrode in a PBS at pH 7 is featureless in the potential range used. Under the same condition, the CV of the Si2.8-G electrode shows a pair of redox peaks at 0 V and 0.1 V, indicating that the particle behaves as a redox species on the graphite surface. The redox peaks could be caused by the particle's interaction with the graphite surface, the nature of the interaction being unclear at the present. As ethanol is introduced to the PBS, the current of the oxidation peak at 0.1 V increases and the peak potential shifts slightly in the positive direction. At higher ethanol concentrations, the oxidation peak current increases further and two new oxidation peaks appear at 0.55 V and 0.8 V. All of the oxidation peak currents increase with further increase in ethanol concentration with the rate for the first peak being slower than those for the other two peaks. It is therefore believed that different catalysis pathways for ethanol at higher potentials are triggered. The same phenomenon has been observed with methanol. FIG. 3D shows the ethanol and methanol calibration curves of the Si2.8-G electrode for the 0.55 V peak obtained with different Si2.8-G electrodes.

Without being bound by any particular theory, it is believed that the silicon nanoparticles promote the electro-oxidation of redox reactants such as renewable fuels, e.g. ethanol, methanol and glucose. The particles may exhibit different catalytic characteristics when immobilized on silicon electrodes and graphite electrodes, suggesting different catalytic pathways as revealed by electrochemical characterization.

In preferred embodiments, the invention provides an electrochemical device comprising a redox reactant and a catalytic composition comprising silicon particles, wherein the silicon particles catalyze a redox reaction of the redox reactant under a low illuminance of from about 0 to about 120 lx, preferably from about 0 to about 80 lx, more preferably from about 0 to about 40 lx, even more preferably from about 0 to about 500 μlx ($10^{-6}$ lux). As known by a skilled person in the art, the lux (symbol: lx) is the SI unit of illuminance and luminous emittance. It is used in photometry as a measure of the intensity of light, with wavelengths weighted according to the luminosity function, a standardized model of human brightness perception.

A light-dependence of the catalytic current has been observed. For example, the particle-immobilized electrodes can generate a large increase in the catalytic oxidation current density when the catalysis is performed in darkness (about 0 to about 50 μlx). The significant increase of catalytic current in darkness provides a unique and convenient way for e.g. enhancing the energy conversion.

In the electrocatalysis of fuel molecules such as methanol, ethanol and glucose, the catalytic current shows a substantial and persistent increase when the catalytic process is performed in darkness as compared to performing the same experiment in room light (about 60 to about 100 lx).

Figure 4:
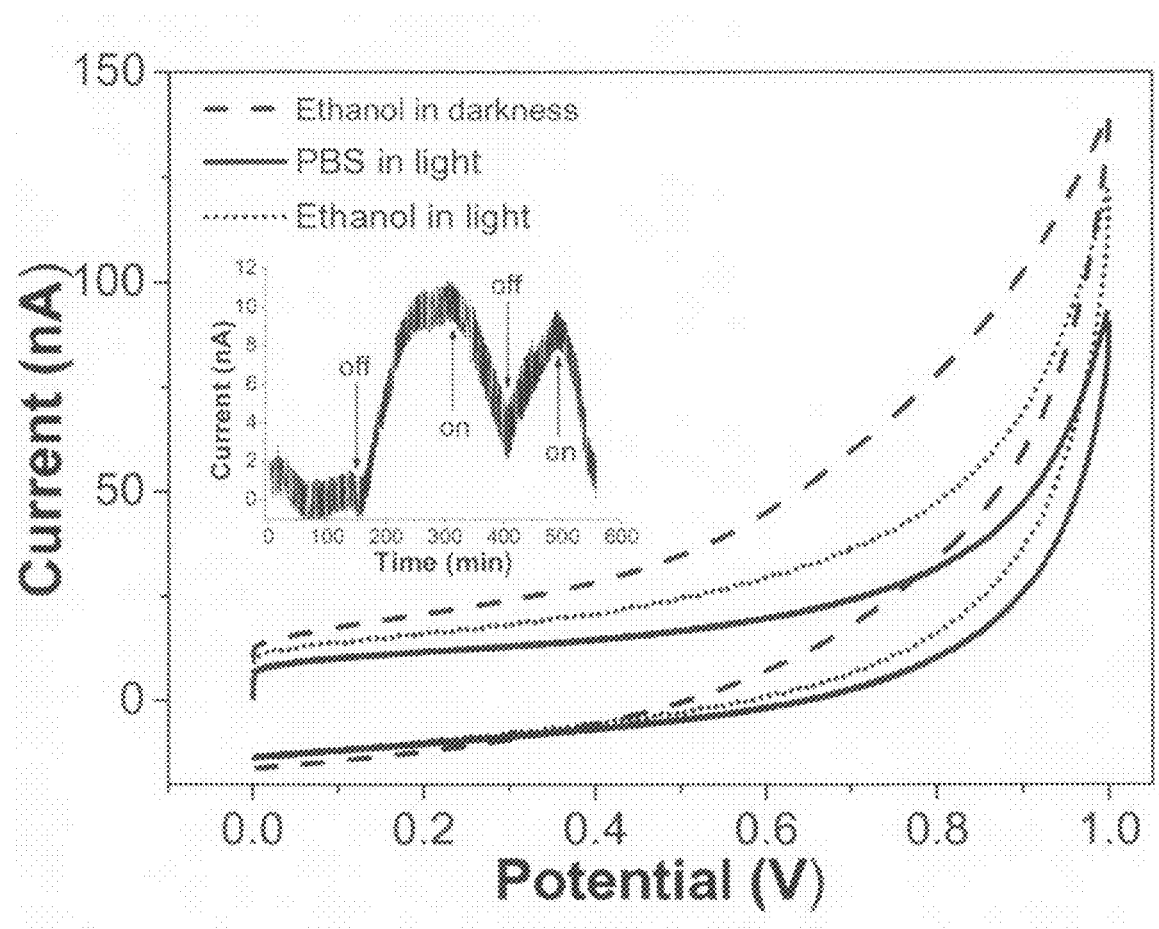
FIG. 4 demonstrates the effect of light illuminance on catalytic current in an embodiment of the invention.

FIG. 4 demonstrates the effect of illuminance such as under light and in darkness on catalytic current. FIG. 4 shows CVs obtained in an ethanol experiment with a Si1-Si electrode in room light and darkness at pH 7. The increase in the catalytic current due to darkness at a potential of 0.8 V is about twice greater than that measured in room light. In FIG. 4, the catalytic current produced by the Si1-Si electrode in 200 mM ethanol at pH 7 shows an increase in darkness. The inset in FIG. 4 is a current-time trace, showing the effect of turning-off and turning-on of the light.

Without the intention to be bound by any particular theory, it is believed that, when the Mott-Schottky model is used to describe the electronic structure of the particle-electrode interface a conducting channel is found to link the particle's electronic orbitals to the bare electrode. As discussed in J. Therrien, *Size dependence of the electrical characteristics of silicon nanoparticles* (University of Illinois Urbana-Champaign, 2002), pp, when the silicon particles are illuminated with white light, excitons are generated with a long recombination lifetime, a characteristic feature of the ultrasmall silicon nanoparticles. Therefore, the "dark" current can be regarded as a fundamental conduction state, in which electrons are transported from the oxidized molecules via the particle to the bare electrode. It is proposed that illumination of light creates excitons within the particle, hence closing the conduction channel for electron transport from the ionized molecules. This may effectively diminishes the "oxidizing ability" of the particle-immobilized electrode resulting in the observed quenching of the oxidation current. The fact that the time constant of the process is long is due to the long recombination lifetime of the exciton, causing a gradual quenching of the oxidation current over time.

Figure 5:
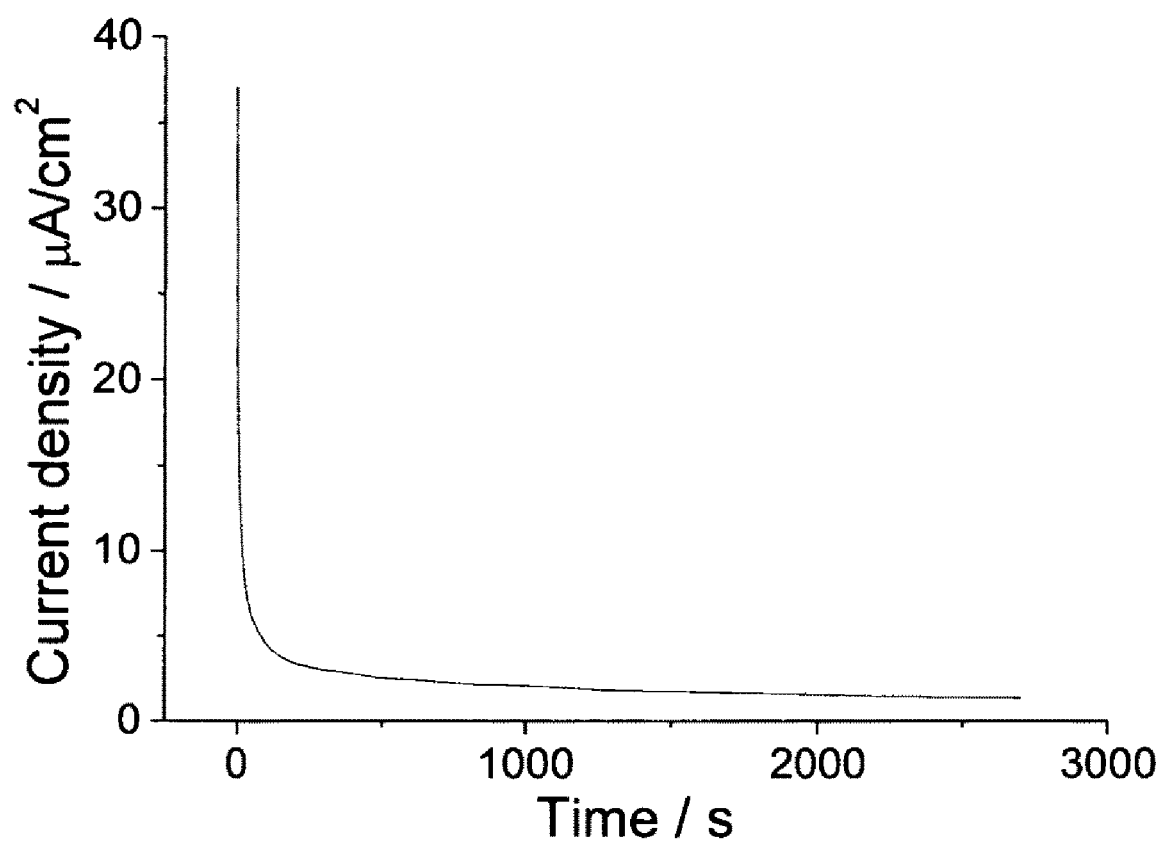
FIG. 5 shows the stability of the particle-immobilized electrode in an embodiment of the invention.

The catalytic oxidation process according to the invention shows good stability. FIG. 5 shows the stability of the particle-immobilized electrode. The oxidation current at a particular potential was observed over time.

As reflected in the electrode's stability, the particle-immobilized electrode does not induce electrode poisoning, which is one of the major problems affecting the performance of fuel cells in prior art.

In exemplary embodiments, silicon nanoparticles of the invention behave as an electrocatalyst for oxidation of ethanol, methanol, and glucose at an electrode. As an inexpensive and non-toxic electrocatalyst, the silicon nanoparticle can be used to develop a commercially viable fuel cell technology compared to using alloys of precious metals as electrocatalysts. In addition, the particle-silicon electrode can be used in the development of all-silicon systems and the light-dependent catalytic current can be used in memory applications.

The invention provides an electrochemical device comprising a redox reactant and a catalytic composition comprising silicon particles, wherein the silicon particles catalyze a redox reaction of the redox reactant. Examples of such device include, but are not limited to, a fuel cell, a sensor, an electrochemical reactor, and a memory.

The particle-immobilized electrode of the invention can be used in the constructions of fuel cells and sensors. For example, when the electrode according to the invention was used as the anode of a fuel cell, it will bring about the oxidation of fuels such as methanol, ethanol or glucose due to its catalytic ability, converting chemical energy to electrical energy.

Figure 6A:
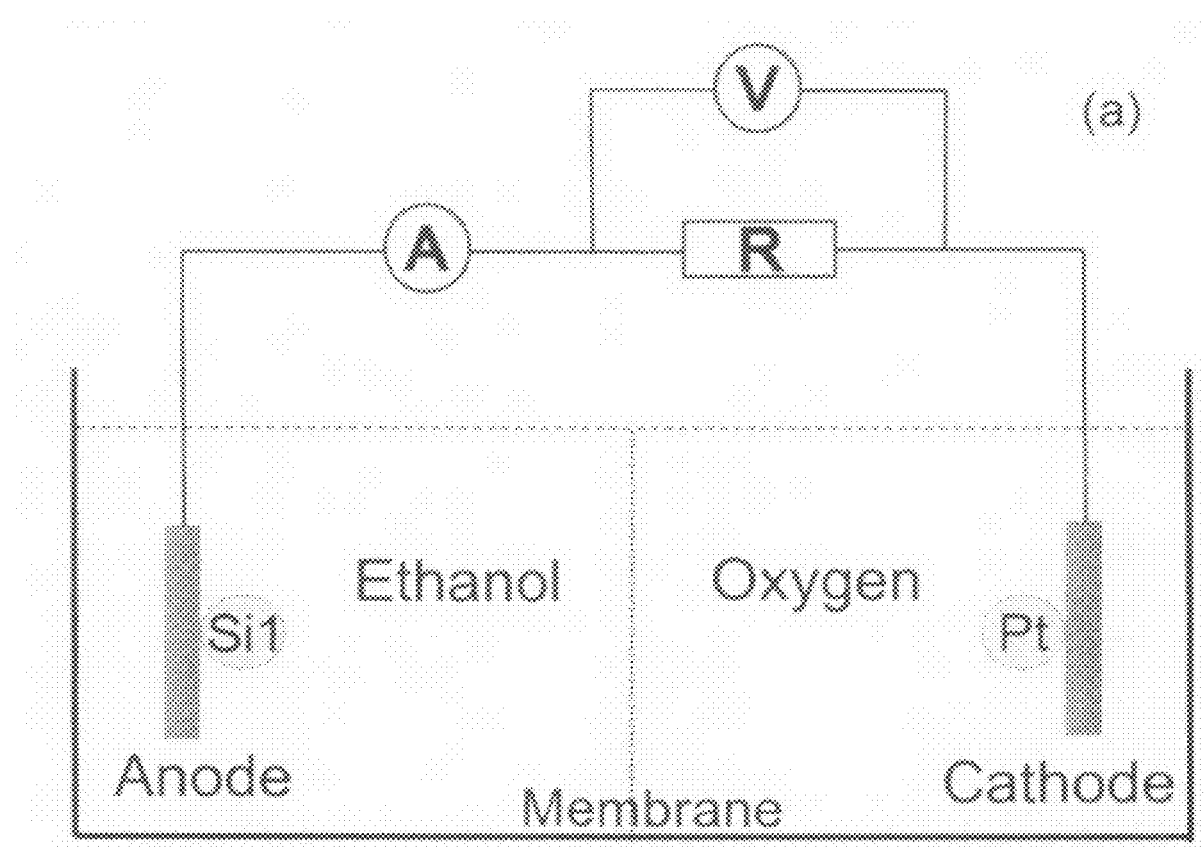
FIGS. 6A-C show the schematic configuration of a two-compartment fuel cell, the power density vs. load resistance curve, and the current vs. voltage curve of the fuel cell in an embodiment of the invention.
Figure 6B:
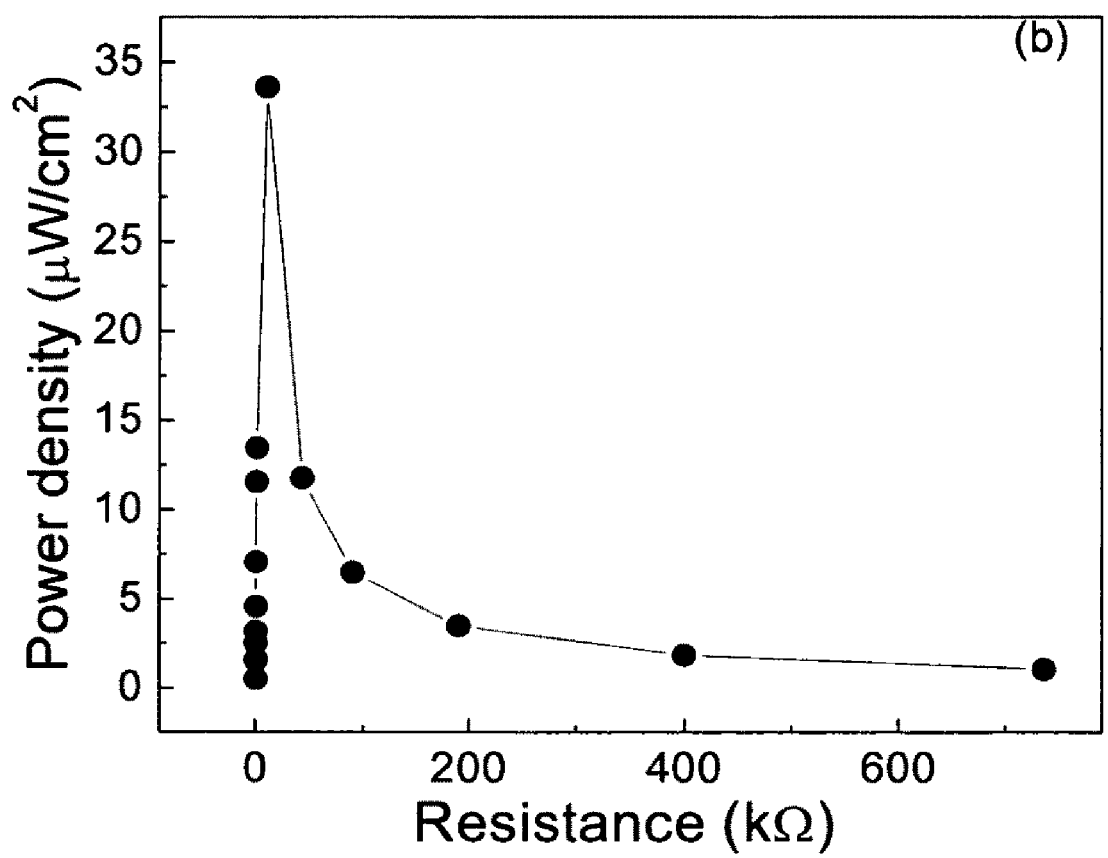
Figure 6C:
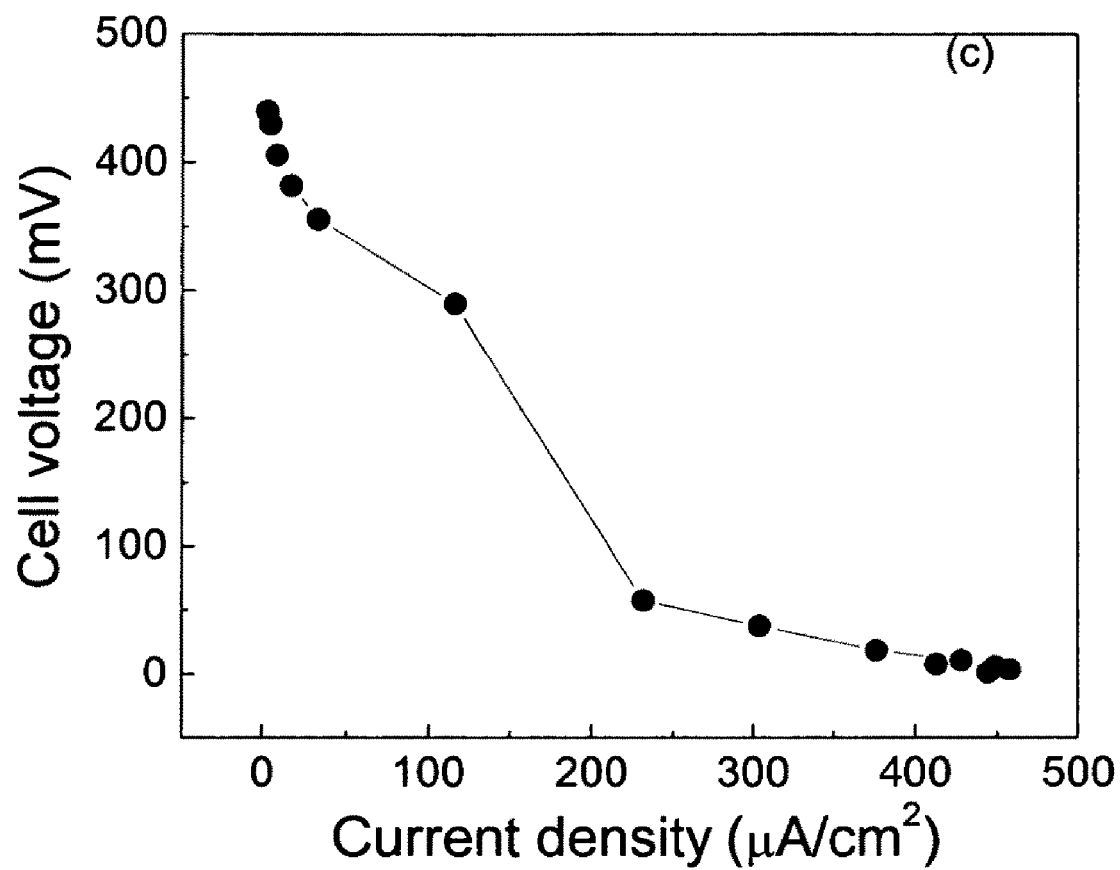

In an exemplary embodiment, a two-compartment direct alcohol fuel cell has been tested. FIG. 6A illustrates a two-compartment direct alcohol fuel cell. In FIG. 6A, A is an ammeter, V is v voltmeter, and R is the load resistance. The anode catalyst, Si1, catalyzes the electro-oxidation of ethanol. The cathode contained a buffer solution, which contained either ambient oxygen or was saturated with oxygen. The cathode catalyst, platinum (Pt), catalyzes the reduction of oxygen dissolved in the solution. Current flows from anode via the external wire to the cathode, delivering power to the load. FIG. 6B shows the plot of power density vs. the value of R; and FIG. 6C shows the plot of the voltage between anode and cathode vs. current density.

Figure 7A:
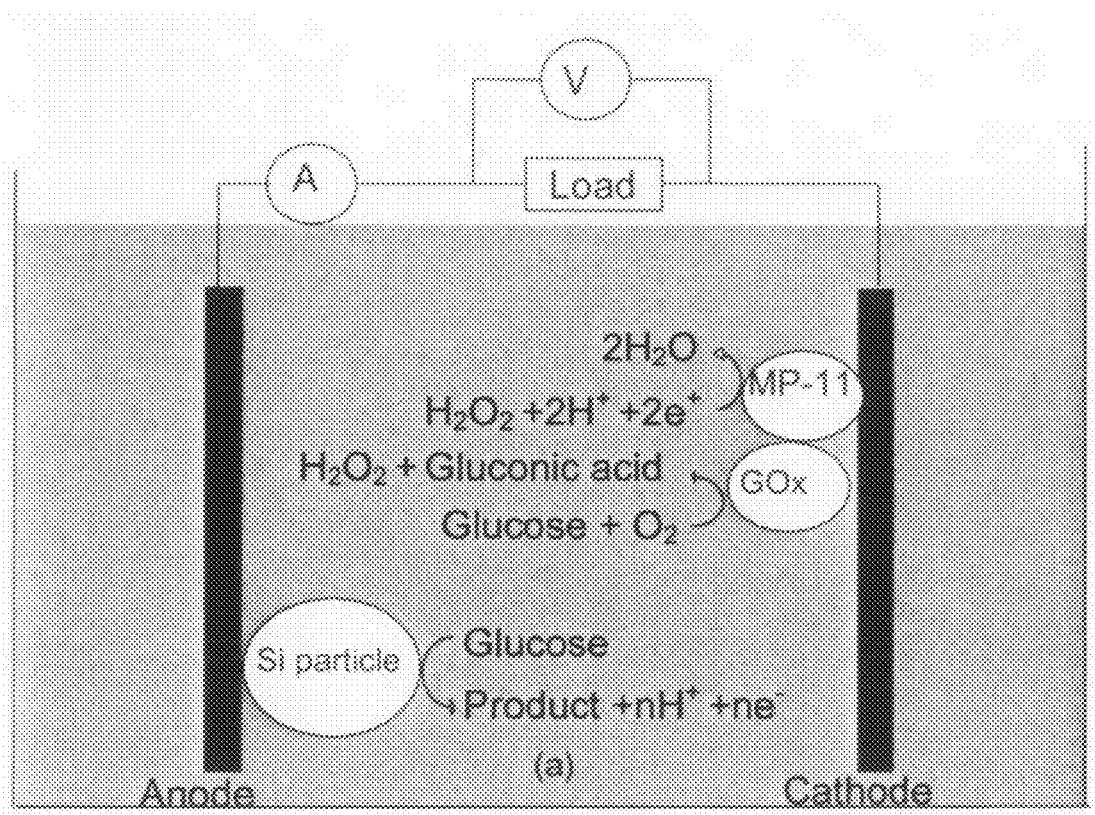
FIGS. 7A-C show the schematic configuration of a single-compartment (membrane-less) fuel cell, the power density vs. load resistance curve, and the current vs. voltage curve of the fuel cell in an embodiment of the invention.
Figure 7B:
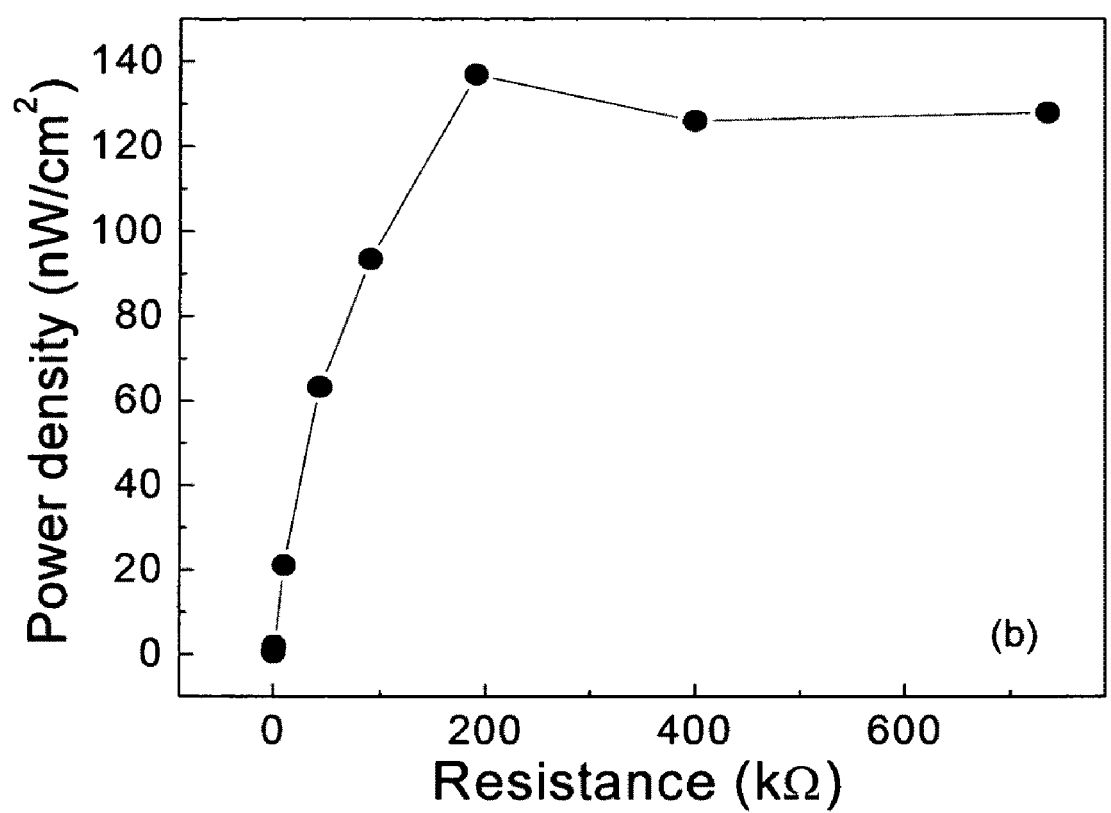
Figure 7C:
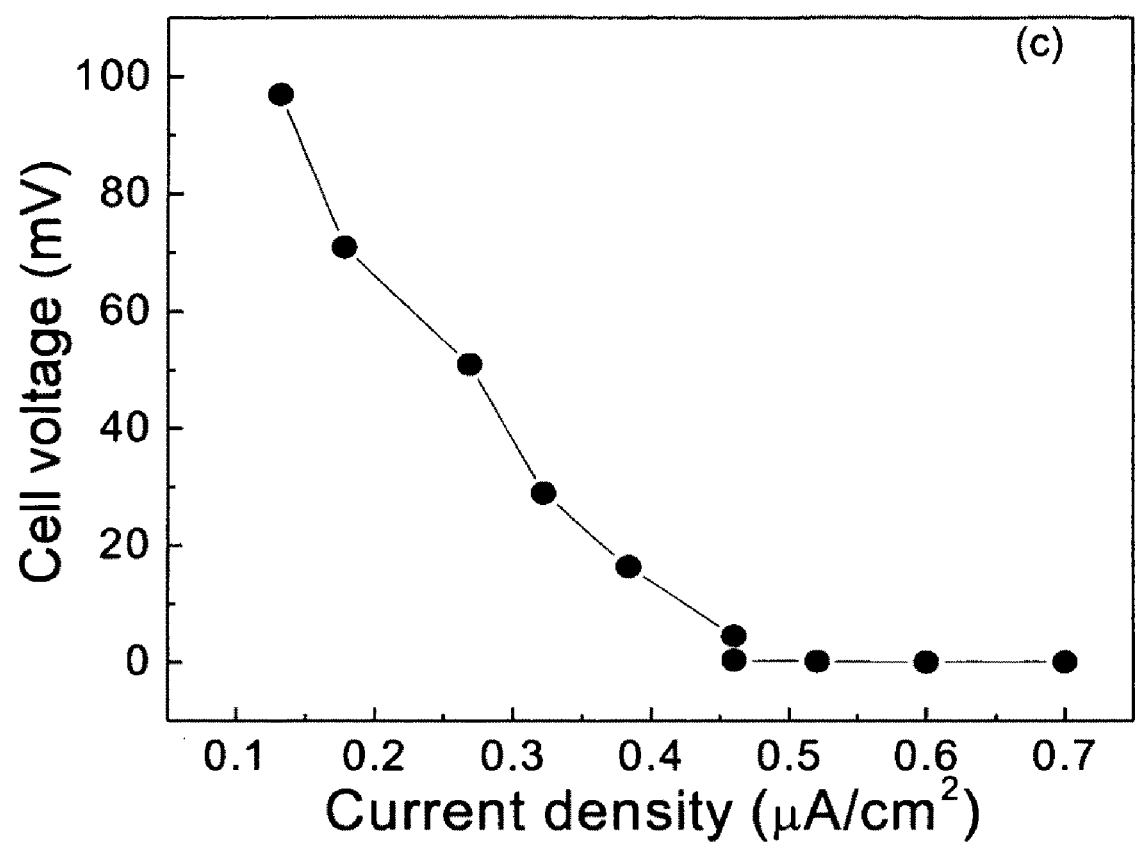

In an exemplary embodiment, a single-compartment (membrane-less) hybrid fuel cell has been tested. Similar to FIG. 6A, FIG. 7A illustrates the device. Glucose was dissolved in the solution as the fuel. The anode catalyst, Si1, catalyzes the oxidation of glucose to produce an unknown number of protons and electrons, which flow into the electrode to generate a current in the external wire. Two enzymes, microperoxidase (MP-11) and glucose oxidase (GOx) were co-immobilized on the cathode electrode. GOx catalyzes the oxidation of glucose to produce $H_2O_2$, which diffuses to MP-11 to be reduced to water using the proton from the anode. Similar to FIGS. 6A and 6B, FIG. 7B shows the plot of power density vs. the value of R; and FIG. 7C shows the plot of the voltage between anode and cathode vs. current density.

The electrode of the invention can also be used as sensors for redox reactants such as methanol, ethanol, and glucose in environmental, biomedical and food/beverage applications.

For the construction of sensors, the silicon nanoparticles can be used to replace enzymes, whose stability is a major issue for long-term implantable applications. Moreover, the silicon nanoparticles are less expensive than enzymes.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. An electrochemical device comprising: a redox reactant; and a catalytic composition comprising silicon particles; wherein the silicon particles catalyze a redox reaction of the redox reactant, and the size of the silicon particles is in the range of from about 0.5 nm to about 100 nm.

2. The electrochemical device according to claim 1, in which the silicon particles comprise colloidal silicon nanoparticles.

3. The electrochemical device according to claim 1, in which the size of the silicon particles is in the range of from about 1 nm to about 2.8 nm.

4. The electrochemical device according to claim 1, in which the silicon particles exhibit visible emission under UV radiation.

5. The electrochemical device according to claim 1, in which the redox reactant comprises one or more organic compounds.

6. The electrochemical device according to claim 5, in which the organic compound is selected from the group consisting of methanol, ethanol, glucose, hydrocarbons, alkane, methane, ketone, 3β-hydroxybutyrate (3β-OHB), phenol, dopamine, lactose, fructose, and mixture thereof.

7. The electrochemical device according to claim 1, which further comprises an electrode.

8. The electrochemical device according to claim 7, in which the electrode comprises an anode, with which the redox reactant is oxidized.

9. The electrochemical device according to claim 7, in which the electrode is selected from a silicon electrode, a graphite electrode, and a carbon paper electrode.

10. The electrochemical device according to claim 7, in which the silicon particles are engaged with the electrode.

11. The electrochemical device according to claim 8, in which the silicon particles are held by bare electrode surface.

12. The electrochemical device according to claim 1, in which the redox reaction is conducted under an illuminance of from about 0 to about 120 lx.

13. The electrochemical device according to claim 1, in which the redox reaction is conducted under an illuminance of from about 0 to about 50 μlx.

14. The electrochemical device according to claim 1, which is selected from a fuel cell, a memory, an electrochemical reactor, and a sensor for detection of the redox reactant.

15. The electrochemical device according to claim 14, in which the fuel cell is a two-compartment fuel cell.

* * * * *